United States Patent [19]

Van Iten

[11] Patent Number: 5,153,971
[45] Date of Patent: Oct. 13, 1992

[54] METHOD OF FORMING A CURVED TAMPON

[75] Inventor: Thomas P. Van Iten, Neenah, Wis.

[73] Assignee: Kimberly-Clark Corporation, Neenah, Wis.

[21] Appl. No.: 798,372

[22] Filed: Nov. 26, 1991

[51] Int. Cl.⁵ .................. D04H 1/22; A61F 13/20
[52] U.S. Cl. ........................ 28/118; 28/120; 604/358; 604/904
[58] Field of Search ............ 28/118, 119, 120, 116; 604/358, 904, 385.1, 378

[56] References Cited

U.S. PATENT DOCUMENTS

| | | | |
|---|---|---|---|
| 1,224,735 | 5/1917 | Gamache et al. | 128/263 |
| 2,458,685 | 1/1949 | Crockford | 28/120 |
| 2,761,449 | 9/1956 | Bletzinger | 28/120 |
| 2,926,394 | 3/1960 | Bletzinger et al. | 28/120 |
| 3,264,691 | 8/1966 | Whitehead | 28/120 |
| 3,340,874 | 9/1967 | Burgeni | 128/285 |
| 3,596,328 | 8/1971 | Voss | 28/120 |
| 3,738,364 | 6/1973 | Brien et al. | 28/120 |
| 3,765,417 | 10/1973 | Crockford | 128/263 |
| 3,811,445 | 5/1974 | Dostal | 28/120 |
| 3,854,481 | 12/1974 | Messing | 128/285 |
| 4,755,166 | 7/1988 | Olmstead | 604/11 |
| 5,047,024 | 9/1991 | Glassman | 604/380 |

FOREIGN PATENT DOCUMENTS 0422660 4/1991 European Pat. Off. ............ 128/285

OTHER PUBLICATIONS

U.S. Ser. No 07/537,677 filed Jun. 14, 1990 to Paul et al. entitled "A Curved Tampon Applicator and a Process for Forming the Applicator and for Assembling an Absorbent Tampon Into Said Applicator".

Primary Examiner—Werner H. Schroeder
Assistant Examiner—Amy Brooke Vanatta
Attorney, Agent, or Firm—54956; Thomas J. Connelly

[57] ABSTRACT

A method of forming a catamential tampon is disclosed which is capable of absorbing menstrual fluids. The method includes the steps of starting with an absorbent having a cross-sectional area of varying thickness. The thickest portion has a greater volume of fibers than the thinnest portion. The absorbent can be optionally enclosed with a cover. An opening is formed through the absorbent and/or cover and a withdrawal string is secured thereto. The absorbent is formed into a generally elongated, cylindrically shaped blank and then is compressed into a pledget having a zone of high density fibers and a zone of low density fibers. After compression, the zone of low density fibers will expand faster and/or to a greater extent than the zone of high density fibers, thereby forming a curved tampon. The curved tampon is rigid and self sustaining and can be used as either a digital tampon or with an applicator.

21 Claims, 4 Drawing Sheets

METHOD OF FORMING A CURVED TAMPON

FIELD OF THE INVENTION

This invention relates to a method of forming a catamenial tampon for absorbing menstrual fluids and, more particularly, to a method of forming a curved tampon having zones of different density fibers which maintain the curvature of the tampon prior to use.

BACKGROUND OF THE INVENTION

Currently, there are two basic types of tampons used for feminine hygiene. The first type is a digital tampon which can be inserted into a woman's vagina by the user's fingers. The second type is a tampon retained in an applicator wherein the tampon is inserted into a woman's vagina via the applicator. Both types of tampons are commonly made by folding or rolling a loosely associated rectangular strip of absorbent material into a blank and then compressing the blank into a cylindrically shaped product known as a pledget. The pledget may or may not have a cover. In both types of tampons, a withdrawal string is attached to the pledget to provide a means for removing the tampon from the woman's vagina. In the applicator style tampon, the tampon is normally assembled into the applicator prior to being wrapped and packaged.

Until now, most tampons have been manufactured having a straight cylindrical profile. Representative samples of pledget tampons are taught in U.S. Pat. Nos. 3,340,874; 3,854,481 and 5,047,024. A disadvantage of a straight profile is that, in the female body, the vaginal cavity is curved, and a woman can experience discomfort when trying to insert a straight tampon into her vagina.

There are patents which teach the use of a curved applicator or stick to facilitate insertion of a straight tampon into a woman's vagina. U.S. Pat. Nos. 1,224,735 and 4,755,166 are representative. However, these various types of applicators still utilize a straight tampon. U.S. Pat. No. 3,765,417 issued to Crockford, and assigned to the present assignee, is one patent which does teach a tampon having an arcuate shape which is designed to be utilized with a curved applicator. This curved tampon is formed by folding a sheet of compressed, absorbent material and has a slight curvature. However, no mention is made of forming a curved tampon, having a generally rigid, cylindrical shape, which could be used alone as a digital tampon or be utilized with an applicator. Furthermore, Crockford does not teach a curved tampon having zones of different density fibers which maintain the curvature of the tampon prior to use.

Now, a method of forming a catamenial tampon has been developed which permits the tampon to have a curvature which corresponds more closely to the curvature of a woman's vagina then a straight tampon.

SUMMARY OF THE INVENTION

Briefly, the present invention relates to a method of forming a catamenial tampon for absorbing menstrual fluids. The method comprises the steps of forming an absorbent with a cross-sectional shape of varying thickness. The thickest portion of the absorbent has a greater volume of fibers than the thinnest portion. The absorbent can optionally be enclosed with a nonwoven cover, and an opening can be formed through both the absorbent and the cover when a cover is utilized. Preferably, the opening is formed adjacent to one end thereof. A withdrawal string is passed through the opening and is secured to the absorbent. The absorbent is then preshaped into a cylindrically shaped blank. The cylindrically shaped blank is then inserted into a mold cavity and compressed into a pledget having a zone of high density fibers and a zone of low density fibers. The pledget is then removed from the mold cavity, and the zone of low density fibers expands at either a faster rate and/or to a greater extent than the high density fibers, thereby forming a curved tampon.

The tampon will maintain its curvature when initially placed within a woman's vagina and will acquire a generally straight, cylindrical shape as it absorbs menstrual fluids, blood, etc. The general object of this invention is to provide a method of forming a catamenial tampon for absorbing menstrual fluids. A more specific object of this invention is to provide a method of forming a curved tampon.

Another object of this invention is to provide a method of forming a curved tampon which is both rigid and self sustaining prior to use.

Still another object of this invention is to provide a method of forming a curved tampon which closely approximates the curvature of a woman's vagina and is rigid enough to be employed as a digital tampon.

Still further, an object of this invention is to provide a simple and economical method of forming a curved tampon.

Other objects and advantages of the present invention will become more apparent to those skilled in the art in view of the following description and the accompanying drawings.

DETAILED DESCRIPTION OF THE PREFERRED EMBODIMENTS

Figure 1:
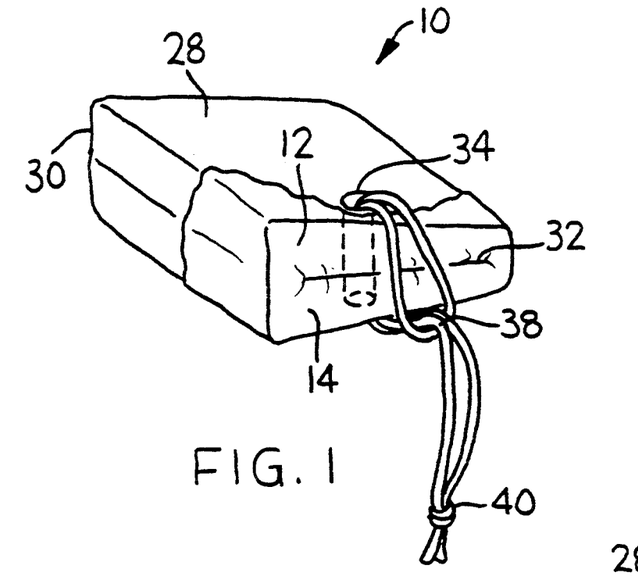
FIG. 1 is a perspective view of a wedge-shaped absorbent enclosed by a cover, which can be used to form a curved tampon, and having a withdrawal string attached thereto.

Referring to FIG. 1, an absorbent 10 is shown which is capable of absorbing menstrual fluids, blood, etc. The absorbent 10 can be formed from any suitable absorbent material made from natural or synthetic fibers, including: cotton, polyester, cellulose, acetate, nylon, polypropylene, rayon or blends thereof. The absorbent can also be a nonwoven, bonded carded web comprised of cotton and rayon fibers. A homogeneous blend of about 50-75 percent bleached cotton linter fibers and about 25-50 percent rayon fibers works well. When a cotton and rayon blend is utilized, the cotton fibers can be of various denier and can be of different lengths. The moisture content of the cotton fibers should be about 10-15 percent. The rayon fibers should have a denier of about 3-8, a staple length of about 1-2 inches (25.4-50.8 mm), and they should also possess high crimp properties. The rayon fibers should most likely have a dull finish. The moisture content of the rayon fibers should be about 10-12 percent.

The absorbent 10 is shown having a wedge-shaped, cross-sectional configuration and is formed by joining two absorbent layers 12 and 14 together. However, it should be noted that the absorbent 10 could be formed into other shapes and can consist of only a single layer of fibers. The absorbent 10 has an overall length of between about 2.5-4.0 inches (63.5-101.6 mm), a width of between about 1-2 inches (25.4-50.8 mm), and a thickness of between about 0.5-1.5 inches (12.7-38.1 mm) at its thickest point, to a thickness of between about 0.125-0.5 (3.2-12.7 mm) inches at its narrowest point.

Figure 2:
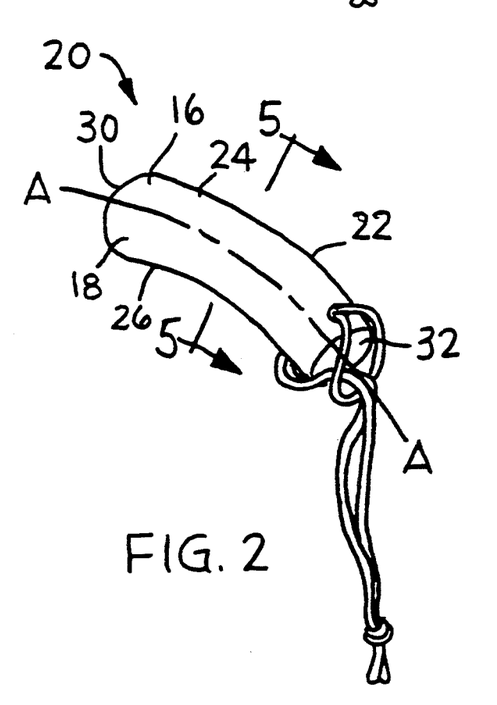
FIG. 2 is a perspective view of a tampon formed from a compressed pledget having a major and a minor radius of curvature and having a zone of high density fibers located adjacent to the major radius of curvature and a zone of low density fibers located adjacent to the minor radius of curvature.

Once the absorbent 10 is compressed, a zone of high density fibers 18 will correspond to the thicker portion of the absorbent 10 and a zone of low density fibers 16 will correspond to the thinnest portion of the absorbent 10, see FIG. 2. The zone of high density fibers 18 will contain a greater volume of fibers than the zone of low density fibers 16.

Referring to FIG. 2, a curved, catamenial tampon 20 is shown having the zones of high and low density fibers, 17 and 18 respectively. The catamenial tampon 20 is arcuate in shape and is capable of absorbing menstrual fluids, blood, etc. which are discharged during a woman's menstrual period. The curved tampon 20 is formed from a compressed pledget 22 having a central longitudinal axis A—A. The central longitudinal axis A—A can be formed on an arc having a radius of curvature of about 3-8 inches (76.2-302.2 mm), preferably about 4-7 inches (101.6-177.8 mm). The central longitudinal axis A—A is flanked by a major radius of curvature 24 and a minor radius of curvature 26. The major radius of curvature 24 is formed on a radius which is larger than the radius on which the minor radius of curvature 26 is formed. Another way of describing the radii of curvature 24 and 26 is that formation of an arc coextensive with the longer outer surface of the tampon 20 is the major radius of curvature 24, and formation of an arc coextensive with the shorter outer surface of the tampon 20 is the minor radius of curvature 26.

The zone of low density fibers 16 is arranged adjacent to the major radius of curvature 24, and the zone of high density fibers 18 is arranged adjacent to the minor radius of curvature 26. Each zone, 16 and 18, occupies at least about 25 percent of the volume of the pledget 22 and preferably occupies at least 40 percent of the volume of the pledget 22. Most preferably, the zone of low density fibers 16 occupies about 60 percent of the volume of the pledget 22, while the zone of high density fibers 18 occupies about 40 percent of the volume of the pledget 22. It should be noted that the particular percent of each zone can vary upon one's particular tampon design and/or manufacturing process. It is also possible to utilize more than two zones if desired.

The zones of high and low density fibers, 18 and 16 respectively, extend over substantially the entire length of the pledget 22 and can be aligned adjacent to one another. However, if desired, the zones 16 and 18 can extend over only a portion of the length of the pledget 22. For example, the zones 16 and 18 can extend over only the central portion of the pledget 22 or extend over only one half of the pledget 22.

Referring again to FIG. 1, the absorbent 10 can optionally be enclosed by a cover 28. The cover 28 can be formed from a nonwoven material such as a polyolefin, particularly polypropylene or polyethylene. A preferred material is spunbond. The cover 28 assures that the fibers of the absorbent 10 do not directly contact the inner wall of a woman's vagina. This prevents fibers from being left behind in the vagina after the tampon 20 has been removed. The cover 28 can be tucked into distally-spaced ends 30 and 32 of the absorbent 10 so as to completely surround and enclose the absorbent fibers. The cover 28 can also be constructed from a heat-sealable material to assist in bonding it to the absorbent 10, such as by heat and/or pressure. It should be noted that other means of attaching the cover to the absorbent fibers can also be used. One example is by the use of an adhesive.

An aperture or opening 34 is formed through the absorbent 10 and also through the cover 28 when it is present. The opening 34 is normally aligned perpendicular to the longitudinal axis A—A of the tampon 20 and adjacent to the distal end 32. A withdrawal string 36 is passed through the opening 34 and is looped upon itself at 38 before the absorbent 10 is preshaped and then compressed into the shape of the pledget 22. A knot 40 is usually formed near the free ends of the withdrawal string 36 to assure that the withdrawal string 36 does not separate from the absorbent 10. The withdrawal string 36 provides a means for removing the tampon 20 from the woman's vagina after the tampon has absorbed a certain amount of menstrual fluids. It should be noted that other means of attaching or fastening the withdrawal string 36 to the absorbent 10 can also be used.

Figure 3:
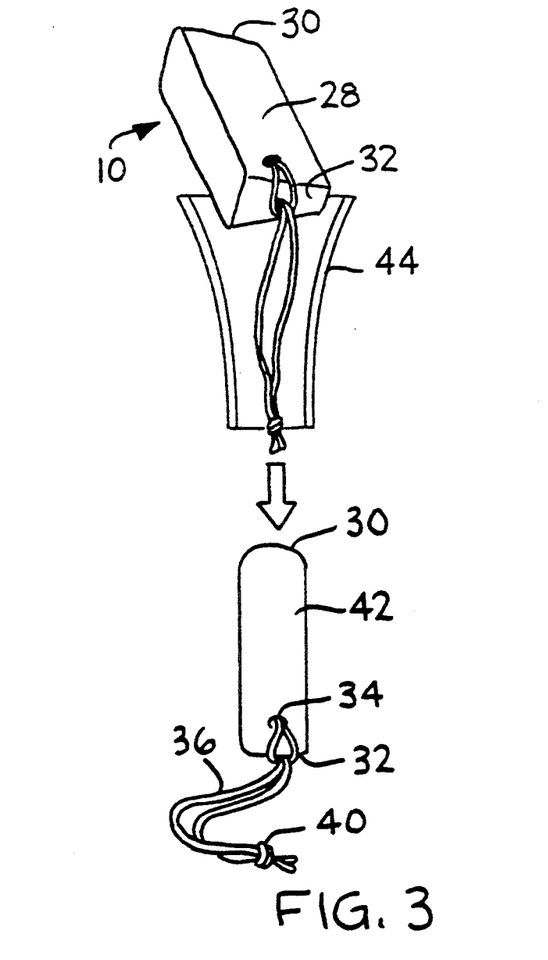
FIG. 3 is an exploded view of the wedge-shaped absorbent shown in FIG. 1 being preshaped into an elongated, cylindrical blank.

Referring to FIG. 3, the method of forming the curved tampon includes preshaping the absorbent 10 into a generally elongated, cylindrical blank 42. One way of accomplishing this is to force the absorbent 10 through a funnel 44 having a diameter which is less than the width of the absorbent 10. The absorbent 10 can be pulled through the funnel by a vacuum, or it can be mechanically pulled or pushed through the funnel 44. The funnel 44 represents the first stage in transforming the wedge-shaped absorbent 10 into a cylindrical shaped blank 42. This transformation can also be visualized as a pre-compression step.

Figure 4:
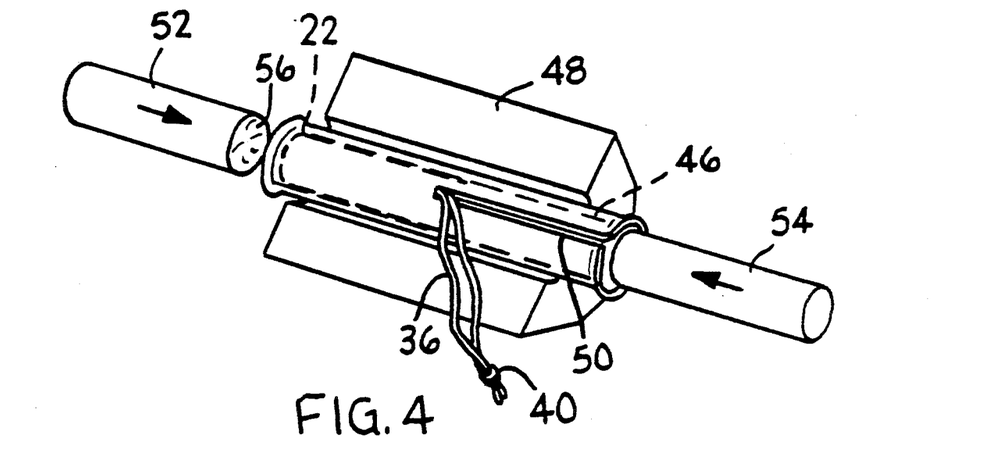
FIG. 4 is a perspective view of a mold cavity in which the cylindrical blank can be compressed into a pledget.

Referring to FIG. 4, the elongated cylindrical blank 42 is then inserted into a mold cavity 46. One example of a mold cavity is a hollow, elongated, cylindrically shaped cavity which is open at both ends. The mold cavity 46 can be heated by means of a heater 48 mounted about its periphery. The mold cavity 46 should contain an axial slot 50 which will permit the withdrawal string 36 and the knot 0 to be positioned outside of the mold cavity 46. With the elongated cylindrical blank 42 positioned within the mold cavity 46, a nose compressor 52 and a base compressor 54 are inserted into opposite ends of the mold cavity 46 and compress the cylindrical blank 42.

The nose compressor 52 is depicted having an insertion end 56 with a concave profile which is capable of forming a rounded tip on the front end 30 of the cylindrical blank 42. The rounding of the front or insertion end 30 of the tampon 20 is optional, but generally is preferred by the ultimate consumer. The cylindrical blank 42 is compressed into a cylindrically shaped pledget 22 having an overall length of between about 1-1.5 inches (25.4-38.1 mm), preferably about 1.25 inches (31.75 mm), and having a diameter from about 0.30-0.75 inches (7.6-19.1 mm). The pledget 22 normally has a weight of between about 2.8-4.2 grams. In forming the pledget 22, it is advantageous to heat the cylindrical blank 42 to an elevated temperature, for example, to a temperature of between about 50°-200° F. (10°-93.3° C., and preferably to between about 90°-110° F. (194°-230° C.). It is also advantageous to maintain the moisture content of the cylindrical blank 42 in a range of between about 5-15 percent, preferably about 10-12 percent.

The cylindrical blank 42 is subjected to an end compression force of between about 750-3,000 lbs. per square inch, preferably, about 1,500-2,000 lbs. per square inch. This pressure will be applied upon the cylindrical blank 42 by the nose compressor 52 and the base compressor 54. The pressure can be applied for a desired period of time, generally for a period of time greater than 0.25 seconds, preferably about 0.25-1.5 seconds. The resulting density of the compressed pledget 22, in the vicinity of the minor radius of curvature, can range from about 10-15 lbs. per cubic foot when the pledget 22 has a moisture content of about 12 percent. The density of the pledget 22, in the vicinity of the major radius of curvature, can range between about 6-10 lbs. per cubic foot when the pledget 22 has a moisture content of about 12 percent.

The pledget 22 is normally straight when it exits the mold cavity 46 but quickly blossoms into a curved-shaped tampon 20. The curved shape is obtained by the expansion of the low density fibers in the zone 16. The fibers in the high density zone 16 tend to retain their compressed shape and, therefore, do not expand, at least not to the same extent nor as rapidly as the fibers in the low density zone 16. The release or expansion of the low density fibers gives the tampon 20 its novel arcuate shape while maintaining a rigid configuration. The rigid configuration permits the tampon 20 to be utilized as a digital tampon which can be inserted into a woman's vagina without the existence of an applicator.

Figure 5:
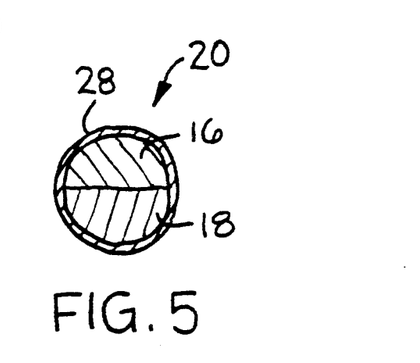
FIG. 5 is a cross-sectional view of the catamenial tampon shown in FIG. 2 taken along line 5—5.

Referring to FIG. 5, a cross-sectional view of the tampon 20 is shown. The area of the zones of high and low density fibers, 18 and 16 respectively, are shown surrounded by the cover 28. It should be noted that, as the fibers in the zone of low density 16 expand outward, the tampon 20 acquires its arcuate shape. As this occurs, the cross-section of the tampon 20 most likely will change from a circular cylinder to a tear-drop or oval-type configuration. This is depicted in FIG. 5. The final cross-sectional configuration of the tampon 20 will be dependent upon the type of fibers used, the amount the fibers are compressed, the moisture content of the fibers, the parameters of the compression step, etc. Once the tampon 20 has been inserted into a woman's vagina, the tampon will absorb menstrual fluid, blood, etc., and the fibers in both the low and the high density zones 16 and 18 will expand. This action will cause the tampon 20 to straighten out into a generally straight, cylindrical shape.

In the manufacturing process, the curved or arcuately shaped tampon 20 can then be packaged to keep it hygienically clean. The package can be made from clear plastic, paper, cellophane, etc. A plurality of these individually wrapped tampons would then be inserted into a package, box or plastic pouch which could then be sold to the consumer.

Figure 6:
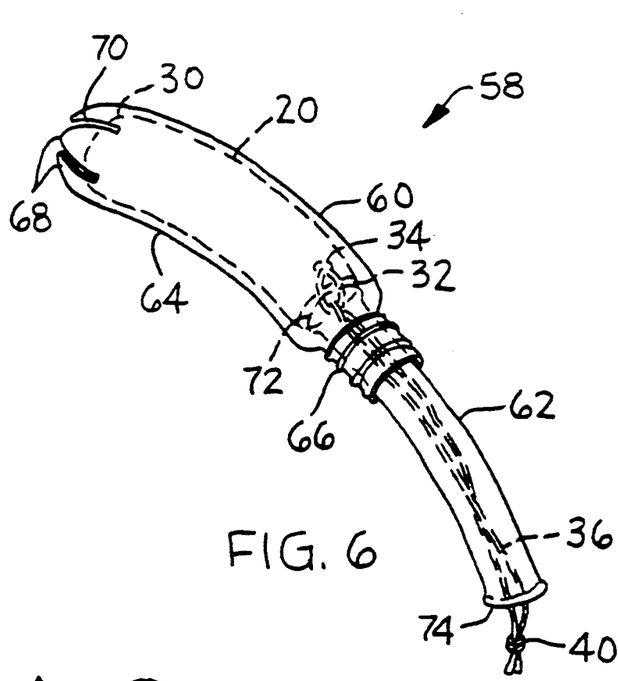
FIG. 6 is a perspective view of a curved tampon retained in an arcuately shaped applicator.

Referring to FIG. 6, instead of wrapping each individual tampons 20, an alternative is to position each tampon 20 into a curved applicator 58. The applicator 58 can include an outer tube 60 and an inner tube 62. The outer tube 60 can be a hollow tube about 2-3 inches long having a diameter of about ¼-¾ of an inch. Preferably, the outer tube 60 is made of a low density polymeric material, such as polyethylene, which can be injection molded. However, it can be constructed out of one or more layers of paper or cardboard, or from a different kind of thermoplastic material or from a blend thereof. Water-dispersible, water-soluble, photodegradable and biodegradable materials should be utilized when possible.

The outer tube 60 can be formed on an arc having a desired radius of curvature and preferably has a stepped outer configuration with an enlarged portion 64 narrowing down to a smaller diameter finger-grip portion 66. The enlarged portion 64 has a generally cylindrical or round cross-sectional shape and is sized to be slightly larger than the outside diameter of the tampon 20, which is retained therein. Petals 68 can be formed on the leading edge of the enlarged portion 64. The petals 68 are thin, flexible members separated by slots or grooves 70. The petals 68 are capable of bending radially outward as the absorbent tampon 20 is expelled from the applicator 58. A plurality of petals 68, preferably an odd number such as 3, 5, 7, etc., should be utilized, since an odd number of petals 68 will prevent the outer tube from collapsing or flattening after the tampon 20 has been expelled. By preventing the outer tube 58 from collapsing, one can be assured that the vaginal tissue will not be pinched. This will assure safe use of the applicator and will contribute to the overall comfort of inserting the tampon 20 into the vagina.

The inner tube 62 is a hollow tube preferably made out of high density polyethylene which can be extruded. The inner tube 62 is shown having an arcuate shape which is similar to the radius of curvature of the outer tube 60. The inner tube 62 is smaller in diameter than the finger-grip portion 66 and can have an oval-shaped, cross-sectional profile if desired. The inner tube 62 has first and second distally spaced flared ends 72 and 74, which prevent the inner tube from separating from the outer tube 60 once it is initially assembled. The inner flared end 72 is designed to push on the flat end 32 of the tampon 20 and expel it from the outer tube 60 into the vagina of a woman. The length of the inner tube 62 is sized relative to the length of the outer tube 60 so that it can perform its function. A description of a tampon applicator is presented in U.S. Ser. No. 07/537,677 filed Jun. 14, 1990, to Paul et al. This patent application is incorporated by reference and made a part hereof.

Once the tampon 20 has been expelled from the applicator 58, the applicator 58 can be properly discarded. While the tampon 20 is within the vagina, it will be capable of absorbing menstrual fluids, blood, body fluids, etc., and the fibers of the tampon 20 will expand as they absorb the fluids. Such expansion will cause the tampon 20 to take on a straighter, more generally cylindrical shape. Once the tampon 20 has served its function, it can be removed by pulling on the withdrawal string 36.

Figure 7:
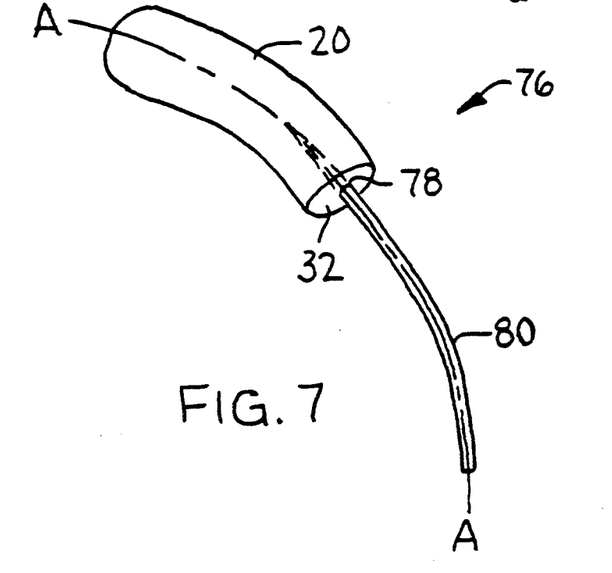
FIG. 7 is a perspective view of a curved tampon having a stick removably inserted into one end thereof which facilitates insertion of the tampon into a woman's vagina.

Referring to FIG. 7, a curved tampon 76 is shown which includes an axial opening 78 formed in one end of the pledget and a curved stick 80 inserted into the axial opening 78. Preferably, the axial opening 78 is formed in the distal end 32 of the tampon 76. The length of the opening 78 can be about 0.25-0.75 inches (6.3-19.5 mm), preferably about 0.625 inches (15.9 mm). The axial opening 78 can be formed in the pledget, as it is being compressed in the mold cavity 46, by inserting a pin into one end of the mold cavity 46. For example, an elongated pin can be formed on the end of the base compressor 54. When the base compressor 54 is removed, the opening 78 is exposed.

One end of the curved stick is inserted into the axial opening 78 formed in the pledget. The stick 80 is shown as curved, but it could also be straight, if preferred. By using a curved stick 80 having a similar arc as the pledget, one can facilitate insertion of the tampon 20 into a woman's vagina in a comfortable fashion. The stick 80 can assist a woman in positioning the tampon 20 into her vagina. Once the tampon 20 is inserted into the vagina, the stick 80 is withdrawn from the opening 78 and can be properly discarded.

Figure 8:
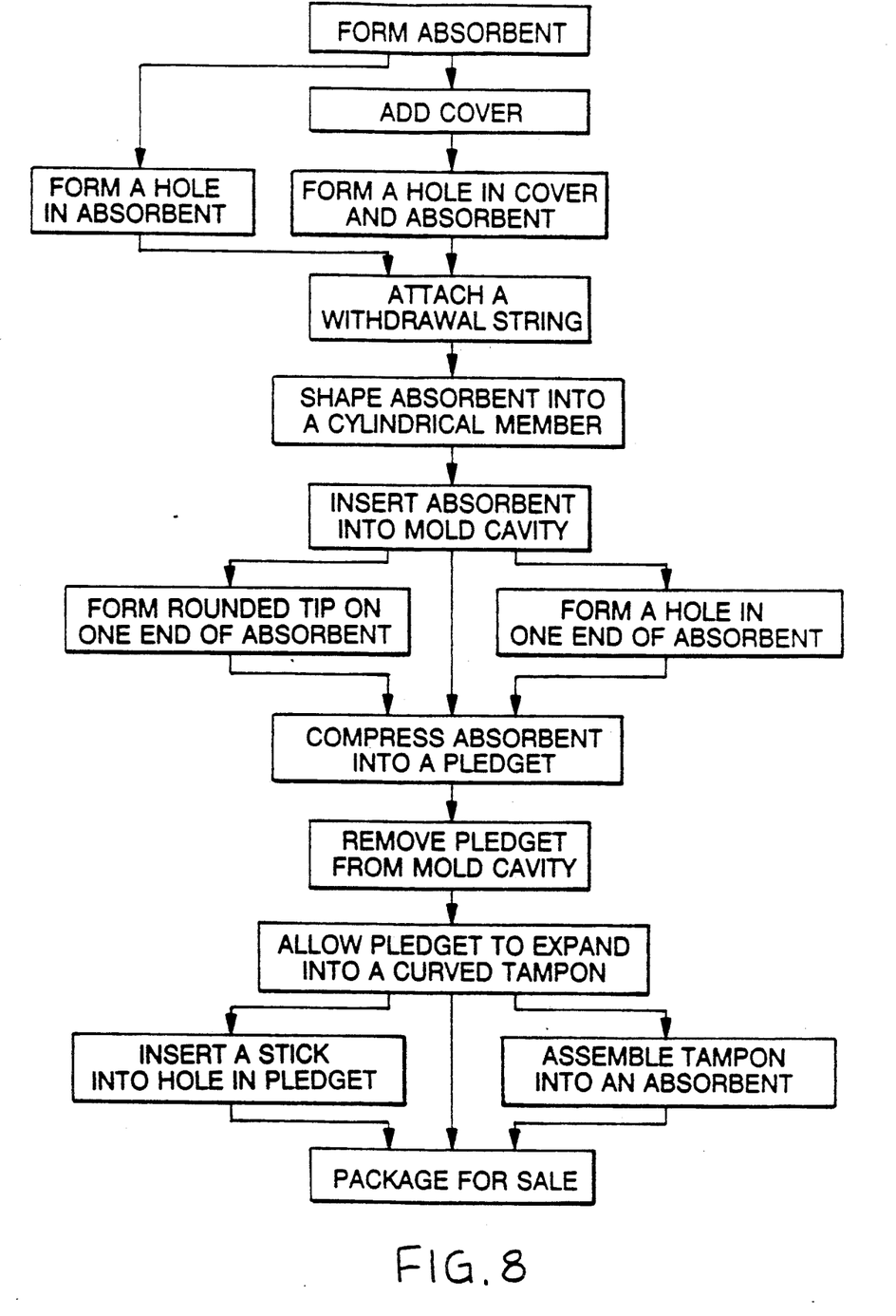
FIG. 8 is a block diagram of a method of forming a curved tampon.

Referring to FIG. 8, a block diagram is depicted which represents the method of forming a curved tampon. One will notice that the block diagram gives some alternatives. The first alternative is that, once the absorbent is formed into a desired shape, it can be enclosed by a cover and have an opening formed through both the cover and the absorbent. Optionally, no cover is needed; in which case, the opening would be formed only in the absorbent itself.

The withdrawal string is then attached and the absorbent is shaped into a cylindrical blank. The cylindrical blank is then inserted into the mold cavity. At this point, one has two more alternatives. One alternative is to form a rounded tip on the insertion end of the pledget. A second alternative is to form an axial opening in the opposite end of the absorbent. An axial opening would be formed if the tampon was to be made into a stick tampon. In this case, after compression, the end of a stick would be inserted into the axial opening to serve as an applicator.

In the mold cavity 46, the cylindrical blank 42 is compressed into a pledget 22. The pledget 22 is then removed from the mold cavity 46 and allowed to expand into a curved tampon 20. The curved tampon 20 can then be packaged and sold as a digital tampon. A second alternative is to assemble the tampon 20 into a tampon applicator such as is shown in FIG. 6. A third alternative is to insert a stick into the axial opening formed in one end of the pledget and form a stick tampon. A plurality of the digital tampons, tampon applicators or stick tampons would then be placed into a package, box or plastic pouch for sale.

While the invention has been described in conjunction with several specific embodiments, it is understood that many alternatives, modifications and variations will be apparent to those skilled in the art in light of the aforegoing description. Accordingly, this invention is intended to embrace all such alternatives, modifications and variations which fall within the spirit and scope of the appended claims.

I claim:

1. A method of forming a curved tampon comprising the steps of:
   a) forming an absorbent with a cross-sectional area of varying thickness, the thickest portion having a greater volume of fibers than the thinnest portion;
   b) securing a withdrawal string to said absorbent;
   c) compressing said absorbent into a generally elongated, cylindrical pledget having a zone of high density fibers and a zone of low density fibers; and
   d) allowing said zone of low density fibers to expand relative to said zone of high density fibers whereby a curved tampon is formed with said curve extending along the length of said tampon.

2. The method of claim 1 wherein in step (a) said cross-sectional area of said absorbent is formed into a wedge.

3. The method of claim 1 wherein said absorbent is compressed at an elevated temperature.

4. The method of claim 3 wherein said elevated temperature is between about 50° to 200° F.

5. The method of claim 1 wherein said absorbent is compressed at a pressure of between about 750 to 3000 pounds per square inch.

6. The method of claim 1 wherein said absorbent is compressed while having a moisture content of between about 5 to 15 percent.

7. The method of claim 1 further comprising positioning said curved tampon into an arcuately shaped tampon applicator which can facilitate insertion of said curved tampon into a woman's vagina.

8. A method of forming a curved tampon comprising the steps of:
   a) forming an absorbent with a wedge-shaped, cross-sectional area of varying thickness, the thickest portion having a greater volume of fibers than the thinnest portion;
   b) enclosing said absorbent with a cover;
   c) forming an opening through both said cover and said absorbent;
   d) passing a withdrawal string through said opening and securing said withdrawal string to said absorbent;
   e) compressing said absorbent into a generally elongated, cylindrical pledget having a zone of high density fibers and a zone of low density fibers; and
   f) allowing said zone of low density fibers to expand relative to said zone of high density fibers whereby a curved tampon is formed with said curve extending along the length of said tampon.

9. The method of claim 8 wherein said opening is formed through the thickness of said absorbent and adjacent to an end thereof.

10. The method of claim 8 wherein said absorbent is compressed at a temperature of between about 90° to 110° F.

11. The method of claim 8 wherein said absorbent is compressed at a pressure of between about 1500 to 2000 pounds per square inch.

12. The method of claim 8 wherein said absorbent is compressed while having a moisture content of between about 10 to 15 percent.

13. A method of forming a curved tampon comprising the steps of:
   a) forming an absorbent with a wedge-shaped, cross-sectional area of varying thickness, the thickest portion having a greater volume of fibers than the thinnest portion;
   b) enclosing said absorbent with a nonwoven cover;
   c) forming an opening through the thickness of said absorbent and adjacent to an end thereof;

d) passing a withdrawl string through said opening and securing said withdrawal string to said absorbent;

e) forcing said absorbent through a funnel to obtain a generally elongated, cylindrical blank;

f) compressing said cylindrical blank in a mold cavity to form a pledget having a zone of high density fibers and a zone of low density fibers; and g) removing said pledge from said mold cavity and allowing said zone of low density fibers to expand relative to said zone of high density fibers whereby a curved tampon is formed with said curve extending along the length of said tampon.

14. The method of claim 13 wherein said funnel has a minimum diameter which is less than the width of said wedge-shaped absorbent.

15. The method of claim 13 wherein said cylindrically shaped absorbent is heated at a temperature of between about 50° to 200° F. while being compressed.

16. The method of claim 13 wherein said cylindrically shaped absorbent has a moisture content of between about 5 to 15 percent.

17. A method of forming a curved tampon comprising the steps of:

a) forming an absorbent from a blend of cotton and rayon fibers, said absorbent having a cross-sectional area of varying thickness, the thickest portion having a greater volume of fibers than the thinnest portion;

b) enclosing said absorbent with a nonwoven cover;

c) piercing both said cover and said absorbent to form an opening through the thickness thereof, said opening being aligned adjacent to an end of said absorbent;

d) forcing said absorbent through a funnel to obtain a generally elongated, cylindrical blank, said funnel having a minimum diameter which is less than the width of said absorbent;

e) inserting said cylindrically shaped blank into a mold cavity and compressing said blank into a pledget having a zone of high density fibers and a zone of low density fibers; and f) removing said pledget from said mold cavity and allowing said zone of low density fibers to expand relative to said zone of high density fibers whereby a curved tampon is formed with said curve extending along the length of said tampon.

18. The method of claim 17 wherein an axial opening is formed in an end of said pledget and a stick is inserted into said axial opening, said stick facilitating insertion of said curved tampon into a woman's vagina.

19. The method of claim 17 further comprising positioning said curved tampon into an arcuately shaped tampon applicator, said applicator facilitating insertion of said curved tampon into a woman's vagina.

20. The method of claim 19 wherein said arcuately shaped tampon applicator includes an inner and an outer tube, and said curved tampon is retained in said outer tube and said inner tube is designed to expel said curved tampon from said outer tube.

21. A method of forming a curved tampon comprising the steps of:

a) forming an absorbent from fibers;

b) securing a withdrawal string to said absorbent;

c) compressing said absorbent into a pledget; and d) causing some of said fibers to expand relative to other fibers whereby a curved tampon is formed with said curve extending along the length of said tampon.

* * * * *

UNITED STATES PATENT AND TRADEMARK OFFICE
CERTIFICATE OF CORRECTION

PATENT NO. : 5,153,971
DATED : October 13, 1992
INVENTOR(S) : Thomas P. Van Iten It is certified that error appears in the above-identified patent and that said Letters Patent is hereby corrected as shown below:

Column 3, line 38, delete "17 and 18" and substitute therefor --18 and 16--.

Column 4, line 63, delete the number "0" and substitute therefor --40--.

Column 5, line 23, add "between" before the word "about".

Claim 13 g), line 9, delete the word "pledge" and substitute therefor --pledget--.

Signed and Sealed this

Twenty-sixth Day of October, 1993

Attest:

BRUCE LEHMAN

*Attesting Officer*  *Commissioner of Patents and Trademarks*